United States Patent [19]

Lorincz et al.

[11] 4,065,458
[45] Dec. 27, 1977

[54] EBURNAMENINE DERIVATIVES

[75] Inventors: Csaba Lórincz; Kálmán Szász; Mária Bolyos; Karola Jovánovics; László Szporny; Egon Kárpati; Éva Pálosi, all of Budapest, Hungary

[73] Assignee: Richter Gedeon Vegyeszeti Gyar Rt., Budapest, Hungary

[21] Appl. No.: 694,204

[22] Filed: June 9, 1976

[30] Foreign Application Priority Data

June 10, 1975 Hungary ................................ RI 566

[51] Int. Cl.² ........................................ C07D 471/22
[52] U.S. Cl. ............................... 260/293.55; 424/256
[58] Field of Search ..................... 260/293.53, 293.55; 424/267

[56] References Cited
PUBLICATIONS

Morrison, et al., "Organic Chemistry," 2nd Ed., Allyn and Bacon, Inc., Boston (1966), p. 683.

Primary Examiner—Henry R. Jiles
Assistant Examiner—R. Ramsuer

Attorney, Agent, or Firm—Karl F. Ross

[57] ABSTRACT

A heart and vasotropic pharmaceutical of the formula:

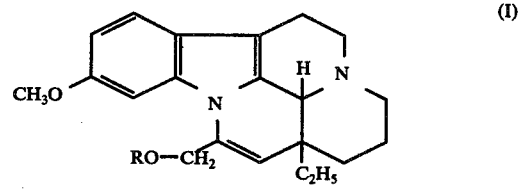

(I)

wherein
R represents a hydrogen atom or an acyl group, preferably a $C_{1-15}$ alkylcarbonyl, $C_{2-6}$ alkenylcarbonyl, or a phenyl- $(C_{1-5})$-alkylcarbonyl group or a benzoyl group optionally substituted with halogen, trihalomethyl, $C_{1-4}$ or nitro
and pharmaceutically acceptable acid addition and quaternary salts thereof.

12 Claims, No Drawings

EBURNAMENINE DERIVATIVES

The invention is directed to the preparation of new eburnamenine derivatives having the following structural formula I and the acid addition salts and quaternary salts thereof

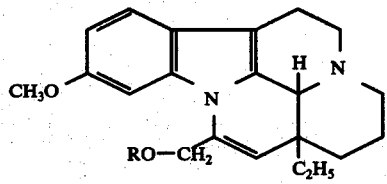

wherein
R is hydrogen or an acyl which can be an alkylcarbonyl group containing 1 to 15 carbon atoms, an alkenylcarbonyl group containing from 2 to 6 carbon atoms or a phenyl alkylcarbonyl group or benzoyl group optionally substituted with halogen or trihalomethyl, $C_{1-4}$ alkoxy or nitro. The eburnamenine derivatives of the invention are pharmaceutically active derivatives of apovincine.

Apovincine is a known compound. The semi-synthetic preparation thereof starting from (−)-11-methoxy-tabersonine is described in the Belgian patent specification No. 765,427 without any reference to the pharmaceutical activity.

Apovincine derivatives according to the invention are all new compounds.

According to pharmacological investigations the compounds of the invention display in the first place a significant heart- and vasotropic effect. This effect can be observed as a vasodilatation, in the blood pressure variation and in the change of the pulse rate.

The pharmacological investigations were carried out in dogs anaesthetized with pentobarbital. The blood circulation of the limb was measured in the femoral artery, the blood circulation of the brain was measured in the internal carotid artery by an electromagnetic rheometer.

The tested compounds were administered intravenously in doses of 1 mg./kg. of body weight and in Table I the average values measured in 5 animals are given. The measured values indicate the difference compared with the situation before the drug administration. Data measured when administering the pharmaceutically active vincamine are also given for comparison.

Table I

| The mean values of changes caused by an intravenous dose of 1 mg./kg. | | | | |
|---|---|---|---|---|
| Substance | 1 | 2 | 3 | 4 |
| (-)-11-methoxy-14-hydroxymethyl-3α,16α-eburnamenine-sodium-hydrogen-sulphate | −16 | +22 | +23 | +25 |
| (-)-11-methoxy-14-acetyl-oxymethyl-3α,16α-eburnamenine-tartrate | −32 | +48 | +47 | +34 |
| (-)-11-methoxy-14-phenylacetyl-oxymethyl-3α,16α-eburnamenine-tartrate | −12 | + 6 | +22 | + 9 |
| (-)-11-methoxy-14(3',4',5'-trimethoxybenzoyl)-oxymethyl-3α,16α-eburnamenine-tartrate | 0 | − 8 | + 3 | + 1 |
| (-)-11-methoxy-14-octanoyloxy-methyl-3α,16α-eburnamenine-tartrate | + 1 | + 2 | + 4 | +11 |
| (-)-11-methoxy-14-propionyl-oxymethyl-3α,16α-eburnamenine-tartrate | −19 | + 4 | +34 | +11 |
| (-)-11-methoxy-14-(4'-chlor-benzoyl)-oxymethyl-3α,16α-eburnamenine-tartrate | −10 | + 1 | + 9 | + 7 |
| (-)-11-methoxy-14-acryloyl-oxymethyl-3α,16α-eburnamenine-tartrate | −19 | + 7 | +18 | +15 |
| (-)-11-methoxy-14-(3'-trifluormethyl-benzoyl)-oxymethyl-3α,16α-eburnamenine-tartrate | − 4 | + 7 | + 5 | + 5 |
| Vincamine | −19 | −17 | + 1 | −19 |

The first column (1) of Table I indicates blood pressure in mm Hg., the second column (2) contains data of measuring the pulse rate per minute, the third column (3) the brain-circulation in ml./minute, and the forth (4) column the limb circulation in ml./minute.

According to Table I, the vasodilatating effects of the new compounds of the invention are superior to that of vincamine. The (−)-11-methoxy-14-hydroxymethyl-3α,16α-eburnamenine sodium hydrogen sulphate and the esters of (−)-11-methoxy-14-hydroxymethyl-3α,16α-eburnamenine with acetic acid, propionic acid and phenyl acetic acid are especially effective.

The compounds possess pharmaceutical utility in that they have an activity in diseases which involves vasoconstriction, in the treatment of atherosclerosis and in supplementary treatment of high blood pressure. The compounds can be used as free bases or as pharmaceutically acceptable acid addition salts or quaternary salts thereof, and can be administered per os, parenterally or rectally. The daily dosage of the products may be varied from 10 to 50 mg. administered in small doses or in time-release form.

The invention is also directed to the preparation of the new eburnamenine derivatives of the formula I and the acid addition and quaternary salts thereof wherein R is hydrogen or an acyl selected from the group consisting of alkylcarbonyl containing 1 to 15 carbon atoms, an alkenylcarbonyl containing 2 to 6 atoms and phenyl alkylcarbonyl and benzoyl unsubstantiated or substituted by halogen, trihalomethyl, $C_{1-4}$ alkoxy or nitro, which comprises reducing apovincine of the formula II

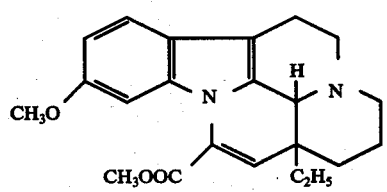

and, if desired, converting the obtained 11-methoxy-14-hydroxymethyl-3α,16α-eburnamenine into an acid addition salt or into a quaternary salt and optionally reacting the obtained product with an acylating agent and, if desired, converting the 11-methoxy-14-acyloxy-methyl-3α,16α-eburnamenine into an acid addition salt or into a quaternary salt.

In the formula I, R is hydrogen or an acyl group. The acyl group may be an alkylcarbonyl group containing 1 to 15 carbon atoms, for example acetyl, propionyl, n-butyryl, is-butyryl, n-valeryl, iso-valeryl, hexanoyl, heptanoyl, octanoyl, nonanoyl, decanoyl, undecanoyl, lauroyl group or an alkenylcarbonyl group containing 2 to 6 carbon atoms, such as acryloyl, metacryloyl, vinylacetyl or crotonoyl group or phenyl-($C_{1-5}$-alkyl)-carbonyl group for example phenylacetyl or phenylpropionyl group, or a benzoyl, chloro, bromo-, or fluorobenzoyl group or a mono-, di- or trimethoxybezoyl or dinitrobenzoyl group.

Among the acid addition salts and quaternary salts of the compounds of the formula I, for example, inorganic acid addition salts may be prepared such as hydrochlorides or hydrobromides, sulphates, preferably hydrogen sulphates such as the potassium hydrogen sulphate or sodium hydrogen sulphate salts. Among the organic acid addition salts preferably tartrate, succinate, citrate or ascorbate salts are prepared. The quaternary salts of the compounds of the Formula I may be prepared from methyl, ethyl, tert.-butyl or benzyl halodes, preferably from the corresponding iodo compound.

(—)-11-Methoxy-14-hydroxymethyl-3α,16α-eburnamenine (R = hydrogen) can be prepared by reducing (+)-apovincine. The reduction is carried out in an organic solvent, preferably in a hydrocarbon of the benzene series or in tetrahydrofuran. As reducing agents preferably complex metal hydrides, for example, lithium aluminum hydride or sodium borohydride, or an organic aluminate such as sodium dihydro-bis(2-methoxy-ethoxy)-aluminate can be used. The reduction is conducted at a temperature −10° to 50° C, preferably at room temperature. The reduction can be monitored by thin layer chromatography. The unreacted reducing agent is decomposed by treating with a suitable agent such as ethyl acetate, whereafter the reaction mixture is evaporated, the residue is dissolved in a diluted aqueous acid, the solution is made alkaline and the latter solution is extracted with a chlorinated hydrocarbon, for example with methylene chloride, chloroform, carbon tetrachloride or dichloroethane.

The extracts are combined and evaporated. The residue is dissolved in an organic solvent mixture, preferably in a mixture benzene and of an aliphatic alcohol of 1 to 5 carbon atoms, and is purified by adsorption, preferably by column chromatography. As the adsorbent preferably silica gel is used. In case of purifying by column chromatography the solvent mixture and the starting eluent contains 90–99%, preferably 95–98% benzene. The starting eluent is used also for removing the unreacted apovincine from the column. The (—)-11-methoxy-14-hydroxymethyl-3α,16α-eburnamenine is eluated with the mixture of benzene and alcohol containing 80–90% of benzene. The eluate fractions containing the product are identified by thin layer chromatography, and the fractions containing the desired compound are combined.

After evaporation and chromatographic purification the product of the reduction is obtained in the form of a base, which may be converted, if desired, into an acid addition salt or quaternary salt.

The salt formation may be carried out directly in the eluate containing the base.

The corresponding acid component may be added to the partially evaporated eluate or to the base obtained after evaporation in the form of a dry residue.

The acid component is generally added to the base or to the partially evaporated eluate containing the base in the form of saturated solution particularly ether or acetone solution.

The acid addition salts are generally formed at pH 3 to 5, preferably 4.

Quaternary salts for example salts obtained from methyl, ethyl, iso-butyl or benzyl halide are prepared by reacting the base dissolved in acetone with the corresponding iodo compound.

When preparing 11-methoxy-14-hydroxymethyl-3α,16α-eburnamenine using optically active apovincine as starting material, the corresponding optically active product is obtained. During the reaction the polarity will be changed in a characteristic way: (—)-11-methoxy-14-hydroxymethyl-3α,16α-eburnamenine is obtained from (+)-apovincine, the polarity of the product remains unchanged in the course of salt formation or acylation.

11-Methoxy-14-acyloxymethyl-3α,16α-eburnamenines of the invention are prepared by acylating the 11-methoxy-14-hydroxymethyl-3α,16α-eburnamenine or an acid addition salt thereof.

As acylating agents, acids can be used which contain the desired acyl group. Acylation is carried out in the presence of an organic solvent preferably of a chlorinated hydrocarbon, particularly methylene chloride, chloroform, and of an acid salt preferably of N,N'-dicyclohexyl-carbodiimide.

The acylation may be carried out at a temperature of 0° to 50° C, preferably at room temperature. N,N'-dicyclohexyl-urea formed as a by-product of the reaction is separated from the reaction mixture by filtration, whereafter the product acylated in 14 position is isolated from the reaction mixture. The product can be isolated by extraction, by evaporation of the reaction mixture and by purification by adsorption, preferably by chromatography.

According to a preferable aspect of present invention as acylating agent an acid anhydride containing the corresponding acyl group can be used. Acylation is carried out in the presence of an organic solvent, preferably of a chlorinated hydrocarbon, preferably methylene chloride or chloroform with stirring at a temperature of 0° to 50° C preferably at room temperature. After the acylation reaction the pH value of the reaction mixture is adjusted to pH 8 to 9 with stirring by adding a solution of diluted alkali metal hydroxide and the phases are separated. The 14-acylated product is contained in the organic solvent phase. The alkalineaqueous phase is extracted with a new portion of solvent, preferably with a chlorinated hydrocarbon, the organic phases are pooled and the acylated product is preferably separated from the mixture by evaporation and chromatographic purification.

According to a further embodiment of the present invention the acylating agent is an acid halide containing the corresponding acyl group. The acylation may be carried out in the presence of water or an organic solvent such as pyridine or a chlorinated hydrocarbon, preferably methylene chloride or chloroform optionally in the presence of an acid binding agent, for example alkali metal hydroxide or alkali metal carbonate. The acylation is conducted at a temperature in the range of from about −30° C to the boiling point of the reaction mixture preferably at −20° to 25° C. After the acylation the mixture is stirred, if desired, for 0.5 to 5 hours and is stored for 2 to 16 hours. After the termination of the reaction the pH-value of the reaction mixture is adjusted by adding water and alkaline metal hydroxide or alkali metal carbonate to 8–9.

When acylating in pyridine, the product can be extracted from the alkalized reaction mixture with chlorinated hydrocarbons preferably with methylene chloride or chloroform. When conducting the acylation in chlorinated hydrocarbons the reaction mixture is allowed to separate. The organic solvent phase containing the product is separated and the alkaline aqueous phase is extracted with a new portion of chlorinated hydrocarbon. The organic phases containing the product are combined and, after removing the water, the mixture is evaporated at reduced pressure.

The dry residue is dissolved in an organic solvent particularly in chlorinated hydrocarbons, in alcohols, in ethyl acetate, in acetone, or preferably in benzene and is purified by an adsorption method such as by chromatography on a column packed with aluminum-(III)-oxide or silicagel as adsorbent. As an eluent an organic solvent, preferably one of the solvents mentioned above, particularly benzene, is used.

The product of the eluate fractions is identified by thin layer chromatography, the eluate fractions containing the product in the form of a base are combined and evaporated. The dry residue is recrystallized if desired. The 14-acylated product is converted, if desired, into an acid addition or into a quaternary salt mentioned above. The salt formation is carried out analogously with the preparation of the salts of 11-methoxy-14-hydroxymethyl-3α,16α-eburnamenine.

The melting points of the compounds according to the invention were determined on a Boetius-appliance, the specific rotation was measured on a Perkin-Elmer-257 polarimeter and the infrared spectrum was determined on a Perkin-Elmer spectrometer. Eluate fractions obtained by column chromatography were identified by thin layer chromatography. Retention factors were measured on silica-gel adsorbent in an eluent system of ethyl acetate-glacial acetic acid-piridine-water = 60:6:20:11 or of chloroform ethyl acetate-methanol = 8:2:1.

Compounds of the general formula I prepared according to the invention as active ingredients can be admixed with pharmaceutically acceptable non-toxic, inert, solid or liquid carriers and/or excipients which are suitable for oral, parenteral or rectal administration and thus pharmaceutical compositions are prepared. As carriers, for example water, gelatin, milk, sugar, pectin, stearic acid or the salt thereof, talcum, vegetable oils, polyalkylene glycols can be used.

As excipients stabilizers, preservatives, wetting and emulgating agents, puffers, flavouring, coloring agents and odorants can be used.

The compositions may optionally contain other pharmaceutically active compounds such as vitamins.

For oral administration the active ingredient is used in the form of tablets, dragees, capsules, solutions, emulsions, syrups, for rectal administration in the form of suppositories and, for injectable administration, as injectable aqueous and oily solutions, emulsions or suspensions.

The compositions can be formed by the conventional methods such as stirring, homogenization, screening, granulation, pressing, dissolving or sterilizing.

The details of the process of the invention further illustrated by the following nonlimiting Examples.

EXAMPLE 1

(−)-11-Methoxy-14-hydroxymethyl-3α,16α-eburnamenine 9.34 g. (0.024 moles) of (+)-apovincine are dissolved in 50 ml. of benzene and 10 ml. of a benzenic solution of sodium-dihydro-bis-(2-methoxy-ethoxy)-aluminate of a concentration of 70% (0.034 moles) are added to the first solution at 20° to 25° C, whereafter the reaction mixture is stirred for 2 hours. The progress of the reduction is monitored by thin layer chromatography. The unreacted reducing agent is decomposed with 10 ml. of ethyl acetate and the reaction mixture is evaporated at reduced pressure, 200 ml. of 2% sulphuric acid are added to the dry residue and the pH value of the mixture obtained is adjusted to a value of 8 to 9. The alkaline aqueous solution obtained is extracted with 4×200 ml. of methylene chloride. The extracts of methylene chloride are pooled, the water is removed with potassium carbonate and the mixture is evaporated at reduced pressure.

The dry residue is dissolved in 10 to 15 ml. of a mixture of benzene: ethanol = 98:2 and the solution is worked up by column chromatography on a silica-gel of a grain diameter of 0.05 to 0.2 mm. manufactured by Merck.

The unreacted (+)-apovincine is eluted with a mixture of benzene: ethanol = 98:2, with the same mixture = 95:5, followed by the eluation of (−)-11-methoxy-14-hydroxymethyl-3α,16α-eburnamenine obtained in the course of the reaction with a mixture of benzene:ethanol = 9:1 then 8:2. During the chromatography eluate fractions of 150 ml. are collected and each fraction was identified by thin layer chromatography. (Adsorbent: silica-gel, eluent system: chloroform-ethyl acetate-methanol = 8:2:1).

The combine fractions containing (+)-apovincine (fractions 10 to 13) and the combined (−)-11-methoxy-14-hydroxymethyl-3α,16α-eburnamenine fractions (15 to 26 fractions) are separately evaporated at reduced pressure.

The recovered (+)-apovincine can be used again. The 6.28 g. of crude (−)-11-methoxy-14-hydroxymethyl-3α,16α-eburnamenine are optionally recrystallized from 20 ml. of cyclohexane.

Yield: 6.08 g. (70.0%) of (−)-11-methoxy-14-hydroxy-methyl-3α,16α-eburnamenine

M.p.: 162°–164° C $R_f$: 0.4

$[\alpha]_D^{20} = -110.3°$ (c = 1, in pyridine)

IR spectrum: 3700, 3200 cm$^{-1}$ ($\nu$OH), 3100, 3000 cm$^{-1}$ ($\nu$CH aromatic), 3000, 2800 cm$^{-1}$ ($\nu$CH$_2$, CH$_3$), 1650, 1612 cm$^{-1}$ (C—C), 1570 cm$^{-1}$ ($\nu$C═C), 1300 cm$^{-1}$ ($\beta$OH), 1025 cm$^{-1}$ ($\nu$C—O/H/) 820 cm$^{-1}$ ($\gamma$CH).

Analysis: Calculated for C$_{21}$H$_{26}$O$_2$N$_2$ Calculated %: C = 74.6; H = 7.7; N = 8.2; O = 9.4; Found %: C = 74.5; H = 7.4; N = 8.1.

EXAMPLE 2

(−)-11-Methoxy-14-hydroxymethyl-3α,16α-eburnamenine 0.65 g. (0.0017 moles) of (+)-apovincine are dissolved in 20 ml. of anhydrous pyridine. A suspension of 0.15 g. (0.0039 moles) of lithium aluminum hydride in tetrahydrofuran are added to the solution at 20° to 25° C and the reaction mixture is stirred for 2 hours. The progress of the reduction is monitored by thin layer chromatography. The unreacted reducing agent is reacted with 7 ml. of ethyl acetate and the reaction mixture is evaporated at reduced pressure. 100 ml. of 2% sulphuric acid and an aqueous sodium hydroxide solution of a concentration of 10% are added to the dry residue until the value of pH achieves the value 8 to 9. The alkaline-aqueous solution thus obtained is extracted with 4 × 50 ml. of chloroform. The extracts are combined, the water is removed with potassium carbonate and evaporated at reduced pressure. The dry residue is worked up by column chromatography as described in Example 1.

Yield: 0.36 g. (60%) of (−)-11-methoxy-14-hydroxymethyl-3α,16α-eburnamenine.

The physical constants of the product are identical with those given in Example 1.

EXAMPLE 3

Acid addition salts and quaternary salts of (−)-11-methoxy-14-hydroxymethyl-3α,16α-eburnamenine a. (−)-11-Methoxy-14-hydroxymethyl-3α,16α-eburnamenine-sodium-hydrogensulphate.

1 g. of (−)-11-methoxy-14-hydroxymethyl-3α,16α-eburnamenine are dissolved in 20 ml. of benzene. A chromatographic column is formed from 50 g. of sodium hydrogen sulphate, 0.5 ml. of water and 50–100 ml. of benzene, and the benzenic solution of (−)-11-methoxy-14-hydroxymethyl-3α,16α-eburnamenine is passed through the column and the acid salt obtained is eluted with 1400 ml. of chloroform. The eluate is evaporated at reduced pressure and recrystallized from ethyl ether.

Yield: 1.2 g. (88.2%) of (−)-11-methoxy-14-hydroxymethyl-3α,16α-eburnamenine-sodium-hydrogen-sulphate M.p.: 100°–150° C $[\alpha]_D^{20} = -41.8°$ (c = 1, on pyridine)

b. (−)-11-Methoxy-14-hydroxymethyl-3α,16α-eburnamenine-citrate

To 0.2 g. of (−)-11-methoxy-14-hydroxymethyl-3α,16α-eburnamenine-citrate ethyl ether saturated with citric acid is added under stirring until the pH value achieves the value of 4. The crystalline solution is stored for 8 hours at a temperature from 0° to 2° C, followed by filtration with 7 to 8 ml. of ethyl ether and by drying.

Yield: 0.18 g. (57.0%) of (−)-11-methoxy-14-hydroxy-methyl-3α,16α-eburnamenine-citrate.

M.p.: 109° to 114° C $[\alpha]_D^{20} = -79.3°$ (c = 1, in pyridine)

c. (−)-11-Methoxy-14-hydroxymethyl-3α,16α-eburnamenine-succinate

A salt of succinic acid is prepared according to the method described in Example 2/b. Yield: 58% of (−)-11-Methoxy-14-hydroxymethyl-3α,16α-eburnamenine-succinate Mp.: 85° to 90° C $[\alpha]_D^{20} = -90.4°$ (c = 1, in pyridine)

d. (−)-11-Methoxy-14-hydroxymethyl-3α,16α-eburnamenine-metho-iodide 0.2 g. (0.00059 moles) of (−)-11-methoxy-14-hydroxymethyl-3α,16α-eburnamenine-metho-iodide are dissolved in 10 ml. of acetone and 0.2 g. (0.014 moles) of methyl iodide are added to the solution. The solution is stored at room temperature for 12 to 24 hours. The formation of the quaternary salt is monitored by thin layer chromatography. (Adsorbent: silica-gel, eluent system: chloroform-ethyl acetate-methanol: 8:2:1). After the reaction is completed the solution is evaporated at reduced pressure, 5 ml. of ethyl ether are added to the dry residue and the mixture is stored for 12 hours at a temperature of 0° to +2° C. The crystalline solution is filtered, washed with 3 to 4 ml. of cooled ethyl ether and dried.

Yield: 0.23 g. (82.0%) of (−)-11-methoxy-14-hydroxymethyl-3α,16α-eburnamenine-metho-iodide.

$R_f = 0.0$ $[\alpha]_D^{20} = 92.9°$ (c = 1, in pyridine)

Analysis: Calculated on the basis of the formula $C_{22}H_{29}O_2N_2J$ Calculated %: C = 55.0; H = 6.0; N = 5.8; O = 6.6; J = 26.5; Found %: C = 55.1; H = 6.0; N = 5.7; O = − ; J = 26.5;

e. (−)-11-Methoxy-14-hydroxymethyl-3α,16α-eburnamenine-tartrate

To 0.2 g (0.00059 moles) of (−)-11-methoxy-14-hydroxymethyl-3α,16α-eburnamenine-tartrate ethyl ether saturated with tartaric acid is added under stirring until the value of pH achieves a value of 4 and the salt obtained is separated as described in Example 3/b.

Yield: 0.22 g. (76%) of (−)-11-methoxy-14-hydroxymethyl-3α,16α-eburnamenine-tartrate.

M.p.: 143° to 148° C $[\alpha]_D^{20} = -96.1°$ (c = 1, in pyridine)

EXAMPLE 4

(−)-11-Methoxy-14-benzoylmethyl-3α,16α-eburnamenine-tartrate 1. g. (0.0029 moles) of (−)-11-methoxy-14-benzoylmethyl-3α,16α-eburnamenine are dissolved in 5 ml. of pyridine followed by adding of 0.5 g. (0.0035 moles) of benzoyl chloride at room temperature. The reaction mixture is stirred for 30 minutes and stored at a dark place at a temperature of 20° to 25° C for 6 hours. 50 ml. of water and aqueous sodium hydroxide solution of a concentration of 10% are added to the solution to adjust the pH to a value of 8 to 9. The alkaline reaction mixture thus obtained is extracted with 3 × 30 ml. of methylene chloride. The methylene chloride extracts containing the product are combined, the water is removed by potassium carbonate and the mixture is evaporated at reduced pressure.

The dry residue is dissolved in 5 to 10 ml of benzene and the benzenic solution is worked up by column chromatography (adsorbent: aluminum-(III)-oxide, eluent: benzene). In the course of chromatographying eluate fractions 30 ml. each are collected and the fractions 4 to 10 containing the (−)-11-methoxy-14-benzoylmethyl-3α,16α-eburnamenine base are identified by thin layer chromatography (adsorbent: silicagel, eluent system: ethyl acetate, glacial acetic acid, pyridine and water = 60:6:20:11).

The fractions containing (−)-11-methoxy-14-benzoylmethyl-3α,16α-eburnamenine are pooled followed by evaporation at reduced pressure. As dry residue 0.78 g. of (−)-11-methoxy-14-benzoylmethyl-3α,16α-eburnamenine are obtained to which ethyl ether saturated with tartaric acid is added until pH=4.

The precipitated tartrate is stored for 12 hours at a temperature of 0° to +5° C, then filtered, washed with ether and dried.

Yield: 0.85 g. (48%) of (−)-11-methoxy-14-benzoylmethyl-3α,16α-eburnamenine-tartrate.

M.p.: 98°–105° C $R_f = 0.77$ $[\alpha]_D^{20} = -69.2°$ (c = 1, in pyridine).

IR spectrum: 3300, 2800 cm$^{-1}$ ($\nu CH_2$, $CH_3$), 1720 cm$^{-1}$ ($\nu CO$ ester), 1620 cm$^{-1}$ ($\nu C=C$), 1280 cm$^{-1}$ ($\nu COC$ ester), 818, 774 cm$^{-1}$ ($\gamma CH$)

Analysis: Calculated on the basis of the formula $C_{32}H_{36}O_9N_2$ Calculated %: C = 64.8; H = 6.1; N = 4.7; O = 24.3; Found %: C = 64.7; H = 6.2; N = 4.7; O = —

EXAMPLE 5

(—)-11-Methoxy-14-(3'-trifluoromethylbenzoyl)-oxymethyl-3α,16α-eburnamenine-tartrate 1 g. (0.0029 moles) of (—)-11-methoxy-14-hydroxymethyl-3α,16α-eburnamenine are dissolved in 20 ml. of methylene chloride. Sodium carbonate is added to the solution in an amount equivalent to the acid released during the formation of the ester followed by adding 0.64 g. (0.033 moles) of m-trifluoromethyl-benzoic acid chloride at a temperature of 20° to 25° C. The mixture is stirred at 20° to 25° C for 2 hours and 20 ml of water and aqueous sodium hydroxide solution of a concentration of 2% are added to the solution to achieve the pH value = 8 to 9. After stirring the mixture for 10 minutes it was allowed to separate in a separating funnel.

The phases are separated, the methylene chloride phase is stored and the aqueous phase is extracted with another 10 ml. of methylene chloride. The methylene chloride phases are combined and the product is obtained as described in Example 4 except that the volume of each eluate fraction collected is 50 ml. The base obtained can be found in fractions 1 to 3.

Yield: 1.62 g. (82.2%) of (—)-11-methoxy-14-(3'-trifluoromethyl-benzoyl)-oxymethyl-3α,16α-eburnamenine-tartrate.

M.p.: 104° to 106° C $R_f$ 0.66

$[\alpha]_D^{20} = -59.8°$ (c = 1, in pyridine).

IR spectrum: 3100, 3000 cm$^{-1}$ ($\nu$CH aromatic), 3000, 2800 cm$^{-1}$ ($\nu$CH$_2$, CH$_3$), 1729 cm$^{-1}$ ($\nu$CO ester), 1615 cm$^{-1}$ ($\nu$C=C), 1338 cm$^{-1}$ ($\nu$C—F), 1250 cm$^{-1}$ ($\nu$COC), 1135 cm$^{-1}$ ($\nu$C—F), 815, 760, 700 cm$^{-1}$ ($\gamma$CH).

Analysis: Calculated for $C_{33}H_{35}N_2F_3O_9$ Calculated %: C = 60.0; H = 5.3; N = 4.2; O = 21.8; F = 8.6; Found %: C = 60.0; H = 5.2; N = 4.4

EXAMPLE 6

(—)-11-Methoxy-14-(4'-chlorobenzene)-oxymethyl-3α,16α-eburnamenine-tartrate

The compound is prepared from (—)-11-methoxy-14-hydroxymethyl-3α,16α-eburnamenine and p-chlorobenzoic acid chloride as described in Example 5.

Yield: 1.48 g. (80%) of (—)-11-methoxy-14-(4'-chlorobenzoyl)oxymethyl-3α,16α-eburnamenine-tartrate M.p: 105° to 110° C $R_f$ = 0.67 (adsorbent: silica-gel, eluent system: chloroform-ethyl acetate-methanol = 8:2:1)

$[\alpha]_D^{20} = -62.3°$ (c = 1, in pyridine).

IR spectrum: 3100, 3000 cm$^{-1}$ ($\nu$CH aromic), 3000, 2800 cm$^{-1}$ ($\nu$CH$_2$, CH$_3$), 1720 cm$^{-1}$ ($\nu$CO, 1615 cm$^{-1}$ ($\nu$C=C), 1270 cm$^{-1}$ ($\nu$COC), 1018 cm$^{-1}$ ($\nu$C—Cl), 850, 812, 760 cm$^{-1}$ ($\gamma$CH).

Analysis: Calculated for $C_{32}H_{35}N_2O_9Cl$ Calculated %: C = 61.2; H = 5.5; N = 4.4; O = 23.0; Cl = 5.6; Found %: C = 61.2; H = 5.6; N = 4.4; Cl = 5.4

EXAMPLE 7

(—)-11-Methoxy-14-acryloyl-oxymethyl-3α,16α-eburnamenine-tartrate

The compound is prepared as described in Example 4 from (—)-11-methoxy-14-hydroxymethyl-3α,16α-eburnamenine and acrylic acid chloride. The base can be found in eluate fractions 2 to 7.

Yield: 1.11 g. (68.8%) of (—)-11-methoxy-14-acryloyl-oxymethyl-3α,16α-eburnamenine-tartrate.

M.p.: 85° to 90° C $R_f$ = 0.74 (adsorbent: silica-gel, eluent system: chloroform-ethyl acetate-methanol = 8:2:1)

$[\alpha]_D^{20} = -65.0°$ (c = 1, in pyridine)

IR spectrum: 3100, 3000 cm$^{-1}$ ($\nu$CH aromatic), 3000, 2800 cm$^{-1}$ ($\nu$CH$_2$, CH$_3$), 1725 cm$^{-1}$ ($\nu$CO ester) 1615 cm$^{-1}$ ($\nu$C=C), 1220 cm$^{-1}$ ($\nu$COC), 810 cm$^{-1}$ ($\gamma$CH).

Analysis: Calculated for $C_{28}H_{34}N_2O_9$ Calculated %: C = 61.9; H = 6.2; N = 5.1; O = 26.6 Found %: C = 62.0; H = 6.3; N = 5.0

EXAMPLE 8

(—)-11-Methoxy-14-(4'-nitrobenzoyl)-oxymethyl-3α,16α-eburnamenine-tartrate

The compound is prepared as described in Example 4 from (—)-11-methoxy-14-hydroxymethyl-3α,16α-eburnamenine and from p-nitro-benzoic acid chloride. The base is in eluate fractions 1 to 6.

Yield: 0.47 g. (50%) of (—)-11-methoxy-14-(4'-nitrobenzoyl)-oxymethyl-3α,16α-eburnamenine tartrate M.p.: 119° to 124° C $R_f$ = 0.67 (adsorbent: silica-gel, eluent system: chloroform-ethyl acetate-methanol = 8:2:1)

$[\alpha]_D^{20} = -60.2°$ (c = 1, in pyridine)

IR spectrum: 3100, 3000 cm$^{-1}$ ($\nu$CH aromatic), 3000, 2800 cm$^{-1}$ ($\nu$CH$_2$, CH$_3$), 1730 cm$^{-1}$ ($\nu$CO ester), 1530 cm$^{-1}$ ($\nu_{as}$NO$_2$), 1350 cm$^{-1}$ ($\nu_s$NO$_2$) 1270 cm$^{-1}$ ($\nu$COC ester), 721, 681 cm$^{-1}$ ($\gamma$CH).

Analysis: Calculated for $C_{32}H_{35}N_3O_{11}$ Calculated %: C = 60.3; H = 5.4; N = 6.6; O = 27.6 Found %: C = 60.3; H = 5.3; N = 6.6

EXAMPLE 9

(—)-11-Methoxy-14-lauroyl-oxymethyl-3α,16α-eburnamenine-tartrate

The compound is prepared from (—)-11-methoxy-14-hydroxymethyl-3α,16α-eburnamenine and lauric acid chloride as described in Example 4. The base is in eluate fractions 1 to 2.

Yield: 0.99 g. (52.5%) of (—)-11-methoxy-14-lauroyl-oxymethyl-3α,16α-eburnamenine-tartrate.

M.p.: 81° to 85° C $R_f$ = 0.79 (adsorbent: silica-gel, eluent system: ethyl acetate-glacial acetic acid-pyridine-water = 60:6:20:11)

$[\alpha]_D^{20} = -54.8°$ (c = 1, in pyridine

IR spectrum: 3000, 2800 cm$^{-1}$ ($\gamma$CH$_2$, CH$_3$, 1740 cm$^{-1}$ ($\nu$CO ester), 1615 cm$^{-1}$ ($\nu$C=C, 1220 cm$^{-1}$ ($\nu$COC ester), 813 cm$^{-1}$ ($\gamma$CH).

Analysis: Calculated for $C_{28}H_{34}N_2O_9$ Calculated %: C = 62.0; H = 6.2; N = 5.1; O = 26.6 Found %: C = 62.2; H = 6.6; N = 5.1

EXAMPLE 10

(—)-11-Methoxy-14-octanoyl-oxymethyl-3α,16α-eburnamenine-tartrate 1 g. (0.0029 moles) of (—)-11-methoxy-14-hydroxymethyl-3α,16α-eburnamenine are dissolved in 10 ml. of pyridine. 0.7 g. (0.004 moles) of caprylic acid chloride are added to the solution at a temperature of 20° to 25° C. After stirring for 2 hours 50 ml. of aqueous sodium hydroxide of a concentration of 2% and 50 ml. of chloroform are added to the solution. The ester obtained in the course of the reaction is dissolved in the chloroform phase followed by a repeated extraction with chloroform. The combined chloroform fractions are reacted with potassium carbonate to remove water and the mixture is evaporated at reduced pressure. The dry residue is worked up as described in Example 4. The caprylic acid ester obtained is in the course of chromatography in eluate fractions 1 to 3.

Yield: 1.06 g. (58.0%) of (—)-11-methoxy-14-octanoyl-oxymethyl-3α,16α-eburnamenine-tartrate.

M.p.: 65°–67° C $R_f$ = 0.80 (adsorbent: silica-gel, eluent system: chloroform-ethyl acetate-methanol = 8:2:1)

$[\alpha]_D^{20}$ = 56.3° (c = 1, in pyridine)

IR spectrum: 3100, 3000 cm$^{-1}$ ($\nu$CH aromatic), 3000, 2800 cm$^{-1}$ ($\nu$CH$_3$, CH$_2$), 1740 cm$^{-1}$ ($\nu$CO ester), 1613 cm$^{-1}$ ($\nu$C=C), 1220 cm$^{-1}$ ($\nu$COC), 810 cm$^{-1}$ ($\gamma$CH).

Analysis: Calculated for C$_{33}$H$_{46}$N$_2$O$_3$ Calculated %: C = 64.5; H = 7.5; N = 4.5; O = 23.4; Found %: C = 64.4; H = 7.5; N = 4.4

EXAMPLE 11

(—)-11-Methoxy-14-(2'-chloro-benzoyl)-oxymethyl-3α,16α-eburnamenine-tartrate

The compound is prepared from (—)-11-methoxy-14-hydroxymethyl-3α,16α-eburnamenine and 2-chlorobenzoic acid chloride as described in Example 10.

The base is in eluate fractions 1 to 6.

Yield: 1.16 g. (62.5%) of (—)-11-methoxy-14-(2'-chloro-benzoyl)-oxymethyl-3α,16α-eburnamenine-tartrate M.p.: 98° to 103° C $R_f$ = 0.81 (adsorbent: silica-gel, eluent system: ethyl acetate-glacial acetic acid-pyridine-water = 60:6:20:11)

$[\alpha]_D^{20}$ = —47.6° (c = 1, in pyridine).

IR spectrum: 3100, 3000 cm$^{-1}$ ($\nu$CH aromatic), 3000, 2800 cm$^{-1}$ ($\nu$CH$_2$, CH$_3$), 1732 cm$^{-1}$ ($\nu$CO ester ), 1612 cm$^{-1}$ ($\nu$C=C), 1250 cm$^{-1}$ ($\nu$COC), 1050 cm$^{-1}$ ($\nu$C—Cl), 812, 750, 610 cm$^{-1}$ ($\gamma$CH).

Analysis: Calculated for C$_{32}$H$_{35}$N$_2$O$_9$Cl Calculated %: C = 61.2; H = 5.5; N = 4.4; O = 23.0; Cl = 5.6 Found %: C = 61.1; H = 5.4; N = 4.5 Cl = 5.7

EXAMPLE 12

(—)-11-Methoxy-14-propionyloxymethyl-3α,16α-eburnamenine-tartrate

The compound is prepared from (-)-11-methoxy-14-hydroxymethyl-3 α,16α-eburnamenine and propionic acid chloride as described in Example 10. The only difference is, that the extraction is carried out with 30 and 15 ml. of chloroform respectively. The base is in eluate fractions 1 to 7.

Yield: 1.1 g. (69.0%) of (-)-11-methoxy-14-propionyl-oxymethyl-3α,16α-eburnamenine-tartrate M.p.: 79° to 84° C $R_f$ = 0.74 (adsorbent: silica-gel, eluent system: ethyl acetate=glacial acetic acid-pyridine-water = 60:6:20:11) $[\alpha]_D^{20}$ = -53.9° (C = 1, in pyridine)

IR spectrum: 3100, 2800 cm$^{-1}$ ($\nu$CH aromatic), (CH$_2$, CH$_3$), 1740 cm$^{-1}$ ($\nu$CO ester), 1612 cm$^{-1}$ ($\nu$C=C), 1218 cm$^{-1}$ ($\nu_{as}$ COC ester), 810, 760 cm$^{-1}$ ($\gamma$CH).

Analysis: Calculated for C$_{28}$H$_{36}$N$_2$O$_9$ Calculated %: C = 61.8; H = 6.6; N = 5.1; O = 26.5; Found %: C = 61.7; H = 6.6; N = 5.0

EXAMPLE 13

(-)-11-Methoxy-14-(3',4',5'-trimethoxy-benzoyl) oxymethyl-3α,16α-eburnamenine-tartrate 1g. (0.0029 moles) of (-)-11-methoxy-14-hydroxymethyl-3α,16α-eburnamenine are dissolved in 15 ml. of pyridine. 0.72 g. (0.003 moles) of 3,4,5-trimethoxybenzoyl-chloride are added to the solution. The reaction mixture is stored at a dark place for 16 hours at a temperature of 20° to 25° C whereafter 40 ml. of chloroform are added. The chloroform mixture is extracted with 3 × 40 ml. of sodium hydroxide solution of a concentration of 2%. The chloroform phase containing the ester is separated, potassium carbonate is added to remove water and the mixture is evaporated at reduced pressure. The dry residue is worked up as described in Example 4 by chromatography. The base is in eluate fractions 2 to 9.

Yield: 0.34 g. (17%) of (-)-11-methoxy-14-(3',4',5'-trimethoxybenzoyl)-oxymethyl-3α,16α-eburnamenine-tartrate.

M.p.: 103° to 107° C $R_f$ = 0.7 (adsorbent silica-gel, eluent system: ethyl acetate-glacial acetic acid-pyridine-water = 60:6:20:11)

$[\alpha]_D^{20}$ = -44.3° (c = 1, in pyridine)

IR spectrum: 3100, 3000 cm$^{-1}$ ($\nu$CH), 3000, 2800 cm$^{-1}$ ($\nu$CH$_2$, CH$_3$), 1720 cm$^{-1}$ ($\nu$CO Ester), 1650 cm$^{-1}$ ($\nu$C=C), 1216 cm$^{-1}$ ($\nu_{as}$ COC ester), 681, 765 cm$^{-1}$ ($\gamma$CH)

EXAMPLE 14

(-)-11-Methoxy-14-phenylacetyl-oxymethyl-3α,16α-eburnamenine-tartrate 1 g. (0.0029 moles) of (-)-11-methoxy-14-hydroxymethyl-3α,16α-eburnamenine are dissolved in 35 ml. of ethanol-free chloroform and 0.8 g. (0.005 moles) of phenyl acetic acid chloride are added under stirring to the solution at a temperature of 20° to 25° C. The reaction mixture is cooled at -14° C and stirred for an hour at the same temperature. 30 ml. of aqueous sodium hydroxide solution of a concentration of 20% are added to the mixture at 20° to 25° C and the mixture is stirred for 10 minutes. The chloroform and the aqueous phase are separated and the aqueous phase is repeatedly extracted with 20 ml. of chloroform. The chloroform extracts containing the ester are combined and the water is removed by adding potassium carbonate followed by evaporation of the mixture at reduced pressure. The dry residue is worked up as described in Example 5. The base obtained is in eluate fractions 1 to 5.

Yield: 1.43 g. (79.8%) of (-)-11-methoxy-14-phenylacetyloxymethyl-3α,16α-eburnamenine-tartrate M.p.: 87° to 90° C $R_f$ = 0.65 (adsorbent: silica-gel, eluent system: ethyl acetate-glacial acetic acid-pyridine-water = 60:6:20:11)

$[\alpha]_D^{20}$ = -49.6° (c = 1, in pyridine)

IR spectrum: 3100, 3000 cm$^{-1}$ ($\nu$CH aromatic), 3000, 2800 cm$^{-1}$ ($\nu$CH$_2$, CH$_3$), 1740 cm$^{-1}$ ($\nu$CO ester), 1615 cm$^{-1}$ ($\nu$C=C), 1220 cm$^{-1}$ ($\nu_{as}$COC ester), 725, 700, 680 cm$^{-1}$ ($\gamma$CH)

Analysis: Calculated for C$_{33}$H$_{38}$O$_9$N$_2$ Calculated %: C = 65.2; H = 6.2; N = 4.6; O = 23.8 Found %: C = 65.1; H = 6.2; N = 4.7

EXAMPLE 15

(-)-11-Methoxy-14-phenylacetyl-oxymethyl-3α,16α-eburnamenine-tartrate 0.2 g. (0.00059 moles) of (-)-11-methoxy-14-hydroxymethyl-3α,16α-eburnamenine and 0.092 g. of phenyl acetic acid and 0.14 g. of N,N'-dicyclohexyl-carbodiimide are dissolved in 3.5 ml. of ethanol-free chloroform. The reaction mixture is stored at room temperature at a dark place for 12 hours and the precipitated N,N'-dicyclohexyl-urea is filtered. The filtrate is evaporated at reduced pressure. 3 ml. of methylene chloride are added to the dry residue and the solution is stored for 5 to 6 hours at a temperature of 0° to 5° C. The quantitatively precipitated N,N'-dicyclohexyl-urea is filtered and the filtrate is evaporated again at reduced pressure. The dry residue is dissolved in 3 to 4 ml. of benzene and chromatographed on an aluminum (III)-oxide adsorbent. The mixture is eluted with benzene and the eluate fractions 10ml. each are identified by thin layer chromatography (adsorbent: silica-gel, eluent system: chloroform-ethyl acetatemethanol = 8:2:1).

The base is isolated from eluate fractions 2 to 4 by evaporation.

Yield: 0.14 g. (50.0%) and the tartrate salt is formed as described in Example 4.

Yield: 0.18 g. (50.0%) of (-)-11-methoxy-14-phenylacetyloxymethyl-3α,16α-eburnamenine-tartrate The physical constants of the product are identical with those of the constants given in Example 14.

EXAMPLE 16

(-)-11-Methoxy-14-acetyl-oxymethyl-3α,16α-eburnamenine-tartrate 1 g. (0.0029 moles) of (-)-11-methoxy-14-hydroxymethyl-3α,16α-eburnamenine are dissolved in 7 ml. of pyridine. 0.45 g. (0.0057 moles) of acetyl chloride are added dropwise to the solution. After stirring the mixture for 1 hour 100 ml of water are added and until the pH value of 8 to 9 aqueous sodium hydroxide solution of a concentration of 10% is added to the mixture. The product is extracted from the alkaline reaction mixture with 3×30 ml. of chloroform, the chloroform phases are combined, the water is removed with potassium carbonate and the mixture is evaporated at reduced pressure. The dry residue is worked up by column chromatography as described in Example 4 except the fact that eluate fractions of 40 ml. are collected. The base is in the first 5 fractions.

Yield: 0.7 g. (63.0%) of (-)-11-methoxy-14-acetyl-oxymethyl-3α,16α-eburnamenine-tartrate M.p.: 96° to 102° C $R_f$ = 0.55 (adsorbent: silica-gel, eluent system: ethyl acetate-glacial acetic acid-pyridine-water = 60:6:20:11)

$[\alpha]_D^{20}$ = -53.0° (c = 1, in pyridine)

IR spectrum: 3100, 3000 cm$^{-1}$ ($\nu$CH aromatic), 3000, 2800 cm$^{-1}$ ($\nu$CH$_2$, CH$_3$), 1740 cm$^{-1}$ ($\nu$CO ester), 1620 cm$^1$ ($\nu$C=C), 1240 cm$^{-1}$ ($\nu_{as}$ COC), 838, 778 cm$^{-1}$ ($\gamma$CH).

Analysis:

Calculated for $C_{27}H_{34}N_2O_9$ Calculated %: C = 61.1; H = 6.4; N = 5.3; O = 27.2 Found %: C = 61.0; H = 6.3; N = 5.4;

EXAMPLE 17

(-)-11-Methoxy-14-acetyloxymethyl-3α,16α-eburnamenine-tartrate 0.2 g. (0.00059 moles) of (-)-11-methoxy-14-hydroxymethyl-3α,16α-eburnamenine are dissolved in 5 ml. of methylene chloride and 0.1 ml of acetic acid anhydride are added dropwise to that solution at 20° to 25° C and the mixture is stirred for 1 hour. 10 ml. of aqueous sodium hydroxide solution of a concentration of 2% are added to the mixture and after stirring for 5 minutes the mixture was poured to a separating funnel and the 2 phases were separated. The methylene chloride phase is separated and the aqueous phase is extracted again with 5 ml. of methylene chloride. The methylene chloride extracts are combined and evaporated at reduced pressure. The dry residue is dissolved in 2 to 4 ml. of benzene and chromatographed on an aluminum (III)-oxide adsorbent. As eluent benzene is used and eluate fractions 10 ml. each are collected which are identified by thin layer chromatography.

(Adsorbent: silica-gel, eluent system: chloroform-ethyl acetate-methanol = 8:2:1). The product is isolated after evaporation of eluate fractions 1 to 4.

Yield: 0.21 g. (93%) of (-)-11-methoxy-14-acetyloxymethyl-3α,16α-eburnamenine) and the tartrate is formed as described in Example 4.

Yield: 0.20 g. (90.0%) of (-)-11-methoxy-14-acetyl-oxymethyl-3α,16α-eburnamenine-tartrate The physical constants of the product are given in Example 16.

EXAMPLE 18

(-)-11-Methoxy-14-(3',5'-dinitro-benzoyl)-oxymethyl-3α,16α-eburnamenine and acid addition salts thereof 2 g. (0.0059 moles) of (-)-11-methoxy-14-hydroxymethyl-3α,16α-eburnamenine are dissolved in alcohol-free chloroform. Sodium carbonate is added to the solution under stirring in an amount equivalent to the acid released during the ester formation whereafter 1.4 g. (0.0061 moles) of 3,5-dinitrobenzoic acid chloride are added at a temperature of 20° to 25° C. After stirring the mixture for 1 hour 15 ml. of aqueous sodium hydroxide solution of a concentration of 2% are added to the mixture followed by stirring for further 5 minutes. The mixture is separated in a separating funnel and the chloroform part is isolated. The aqueous phase is extracted with 15 ml. of chloroform and the chloroform phase is isolated and combined with the chloroform phase obtained in the previous step. The water is removed with potassium carbonate from the combined fractions and the mixture is evaporated at reduced pressure. The dry residue is dissolved in 10 to 15 ml. of a mixture of benzene:butanol = 98:2 and worked up by column chromatography (adsorbent: silica-gel of a grain diameter: 0.05 to 0.2 mm, manufactured by Merck, eluent: benzene:ethanol = 98:2). In the course of chromatography eluate fractions 40 ml. each are collected, which are identified by thin layer chromatography.

(Adsorbent: silica-gel, eluent: chloroform-ethyl acetatemethanol = 8:2:1). The product is in eluate fractions 3 to 7, which are combined and evaporated at reduced pressure. The crude product of a weight of 1.39 g. are recrystallized from 10 ml. of cyclohexane and the precipitated crystalline substance is stored for 12 hours at a temperature of 0° to +5° C, followed by filtration, washing with 10 to 15 ml. of cyclohexane and drying.

Yield: 1.23 g. (39.0%) of (-)-11-methoxy-14-(3',5'-dinitrobenzoyl)-oxymethyl-3α,16α-eburnamenine.

M.p.: 160° to 162° C $R_f = 0.59$ $[\alpha]_D^{20} = -90.8°$ (c = 1, in pyridine)

IR spectrum: 3100, 3000 cm$^{-1}$ ($\nu$CH aromatic), 3000, 2800 cm$^{-1}$ ($\nu$CH$_2$, CH$_3$), 1721 cm$^{-1}$ ($\nu$C=O), 1545 cm$^{-1}$ ($\nu_{as}$ NO$_2$), 1347 cm$^{-1}$ ($\nu_s$ NO$_2$), 1275 cm$^{-1}$ ($\nu_{as}$ COC), 1165 cm$^{-1}$ ($\nu_s$ COC), 807, 732, 721 cm$^{-1}$ ($\gamma$CH).

Analysis: Calculated for C$_{28}$H$_{28}$N$_4$O$_7$ Calculated %: C = 63.1; H = 5.2; N = 10.5; O = 21.1; Found %: C = 63.2; H = 5.3; N = 10.4; O = —

0.2 g. of (-)-11-methoxy-14-(3',5'-dinitro-benzoyl)-oxymethyl-3α,16α-eburnamenine are dissolved in acetone and ascorbic acid dissolved in acetone of a concentration of 90% are added to the solution until the pH value = 4, the precipitated ascorbic addition salt is filtered, washed with acetone and dried.

Yield: 0.15 g. (56%) of (-)-11-methoxy-14-(3',5'-dinitrobenzoyl) -oxymethyl-3α,16α-eburnamenine-ascorbic acid salt.

M.p.: 153°-157° C $[\alpha]_D^{20} = -41.0°$ (c = 1, in pyridine)

An acid addition salt can be prepared from 0.2 g. of (-)-11-methoxy-14-(3',5'-dinitro-benzoyl-oxymethyl-3α,16α-eburnamenine as described above.

Yield: 0.19 g. (89%) of (-)-11-methoxy-14-(3',5'-dinitro-benzoyl)-oxymethyl-3α,16α-eburnamenine-hydrochloride.

M.p.: 190°-196° C $[\alpha]_D^{20} = -104.2°$ (c = 1, in pyridine)

EXAMPLE 19

(-)-11-Methoxy-14-(3'5'-dinitrobenzyol)-oxymethyl-3α,16α-eburnamenine-metho-iodide 0.15 g. (0.00028 moles) of (-)-11-methoxy-14-(3',5'-dinitrobenzoyl)-oxymethyl-3α,16α-eburnamenine are dissolved in 6 ml. of acetone and 0.1 g. (0.0007 moles) of methyl iodide are added to the solution. The solution is stored for 6 hours at 20° to 25° C, the progress of the salt formation is monitored by thin layer chromatography. After the termination of the reaction the mixture is stored for 12 hours at a temperature of 0° to 2° C, whereafter the crystalline solution is filtered, washed with 3 to 4 ml. of chilled acetone and dried.

Yield: 0.17 g. (89%) of (-)-11-methoxy-14-(3',5'-dinitrobenzoyl)-oxymethyl-3α,16α-eburnamenine-metho-iodide $R_f = 0.0$ (adsorbent: silica-gel, eluent system: chloroformethyl acetate-methanol = 8:2:1)

$[\alpha]_D^{20} = -94.0°$ (c = 1, in pyridine)

Analysis: Calculated for C$_{29}$H$_{31}$N$_4$O$_7$J Calculated %: C = 51.6; H = 4.6; N = 8.3; O = 16.6; J = 18.8 Found %: C = 51.6; H = 4.6; N = 8.3; J = 18.8

We claim:

1. A compound of the formula

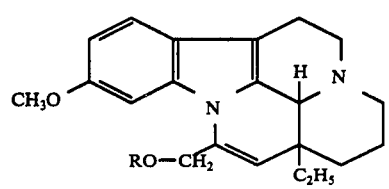

(I)

wherein

R is hydrogen or a C$_{1-15}$ alkylcarbonyl, C$_{2-6}$ alkenylcarbonyl, or a phenyl-(C$_{1-5}$)-alkylcarbonyl or a benzoyl group unsubstituted or substituted with halogen, trihalomethyl, C$_{1-4}$ alkoxy or nitro or a pharmaceutically acceptable acid addition and quaternary salt.

2. The compound defined in claim 1 selected from the group which consists of (-)-11-methoxy-14-hydroxymethyl-3α,16α-eburnamenine and the pharmaceutically acceptable addition salts and quaternary salts thereof.

3. The compound defined in claim 1 selected from the group which consists of (-)-11-methoxy-14-(3'-trifluoromethyl-benzoyl)-oxymethyl-3α,16α-eburnamenine and the tartrate thereof.

4. The compound defined in claim 1 selected from the group which consists of (-)-11-methoxy-14-(4'-chlorobenzoyl)-oxymethyl-3α,16α-eburnamenine and the tartrate thereof.

5. The compound defined in claim 1 selected from the group which consists of (-)-11-methoxy-14-acryloyloxymethul-3α,16α-eburnamenine and the tartrate thereof.

6. The compound defined in claim 1 selected from the group which consists of (-)-11-methoxy-14-lauroyloxymethyl-3α,16α-eburnamenine and the tartrate thereof.

7. The compound defined in claim 1 selected from the group which consists of (-)-11-methoxy-14-octanoylmethyl-3α,16α-eburnamenine and the tartrate thereof.

8. The compound defined in claim 1 selected from the group which consists of (-)-11-methoxy-14-propionyloxymethyl-3α,16α-eburnamenine and the tartrate thereof.

9. The compound defined in claim 1 selected from the group which consists of (-)-11-methoxy-14-(3',4',5'-trimethoxy-benzoyl)-oxymethyl-3α,16α-eburnamenine and the tartrate thereof.

10. The compound defined in claim 1 selected from the group which consists of (-)-11-methoxy-14-phenylacetyl-oxymethyl-3α,16α-eburnamenine and the tartrate thereof.

11. The compound defined in claim 1 selected from the group which consists of (-)-11-methoxy-14-acetyloxymethyl-3α,16α-eburnamenine and the tartrate thereof.

12. The compound defined in claim 1 selected from the group which consists of (-)-11-methoxy-14-(3',5'-dinitro-benzoyl)-oxymethyl-3α,16α-eburnaminenine and the pharmaceutically acceptable acid addition salts and quaternary salts thereof.

* * * * *